United States Patent
Floyd

(10) Patent No.: US 10,143,640 B2
(45) Date of Patent: Dec. 4, 2018

(54) FLUORESCENCE PLAQUE-DISCLOSANT FOR DETECTING DENTAL PLAQUE

(71) Applicant: FLOSS MY HEART, LLC, Dallas, TX (US)

(72) Inventor: Janet L. Floyd, Dallas, TX (US)

(73) Assignee: FLOSS MY HEART, LLC, Dallas, TX (US)

(*) Notice: Subject to any disclaimer, the term of this patent is extended or adjusted under 35 U.S.C. 154(b) by 0 days.

(21) Appl. No.: 14/485,132

(22) Filed: Sep. 12, 2014

(65) Prior Publication Data

US 2015/0079008 A1 Mar. 19, 2015

Related U.S. Application Data

(60) Provisional application No. 61/877,697, filed on Sep. 13, 2013.

(51) Int. Cl.
*A61K 8/46* (2006.01)
*A61Q 11/00* (2006.01)
*A61K 8/49* (2006.01)

(52) U.S. Cl.
CPC .............. *A61K 8/466* (2013.01); *A61K 8/498* (2013.01); *A61Q 11/00* (2013.01); *A61K 2800/43* (2013.01); *A61K 2800/434* (2013.01); *A61K 2800/81* (2013.01)

(58) Field of Classification Search
CPC .... A61K 8/466; A61K 8/498; A61K 2800/43; A61K 2800/434; A61K 2800/81; A61Q 11/00
USPC .................................................. 424/9.71, 49
See application file for complete search history.

(56) References Cited

U.S. PATENT DOCUMENTS

| | | | | |
|---|---|---|---|---|
| 5,862,559 A | * | 1/1999 | Hunter | A46B 7/08 15/167.1 |
| 7,479,268 B2 | * | 1/2009 | Deppe | A61K 8/0216 424/49 |
| 2011/0318713 A1 | * | 12/2011 | Binner | A61C 17/221 433/216 |

* cited by examiner

*Primary Examiner* — Lezah Roberts
(74) *Attorney, Agent, or Firm* — Edwin S. Flores; Chalker Flores, LLP

(57) ABSTRACT

The present invention provides a glow in the dark staining agent for staining dental plaque includes a first plaque-disclosant comprising a fluorophore having an fluorescence emission after being exposed to a light source, wherein the fluorophore adheres to tooth plaque; and a second plaque-disclosant comprising a dye particle that adheres to tooth plaque and is visible.

2 Claims, No Drawings

FLUORESCENCE PLAQUE-DISCLOSANT FOR DETECTING DENTAL PLAQUE

CROSS-REFERENCE TO RELATED APPLICATIONS

This application claims priority based on U.S. Provisional Application No. 61/877,697, filed Sep. 13, 2013. The contents of which is incorporated by reference in its entirety.

TECHNICAL FIELD OF THE INVENTION

The present invention relates in general to the field of plaque-disclosants, specifically to compositions of matter and methods of making and using plaque-disclosants that are fluorescent for the detection of plaque on the surfaces of teeth.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

It is well established that it is difficult to induce adults and children to brush their teeth on a regular basis. The reasons for this vary from inconvenience and time consuming, to sensitivity and a lack of importance. In addition, children that do not brush from an early age do not develop an appreciation of the benefits of regular brushing. In addition, many people do not understand the importance of brushing. These factors contribute to tooth pain, decay, and eventually to the possibility of loss of teeth. As a result it is important to remove the plaque from the teeth which can be accomplished by acquiring a good brushing technique. It is especially important to detect and remove dental plaque. In an effort to remove plaque from the teeth it is necessary to detect plaque deposits on the teeth. For example, a visible indicator allows detection of areas at which dental cleaning effort should be concentrated. Such plaque deposits can be difficult to detect on the teeth by visual inspection without an indicator. Staining agents for making visible dental plaque are known in the form of solutions, tablets, toothpaste, and gels.

For example, U.S. Pat. No. 3,723,613, discloses a staining agent in tablet form that contains FDC Blue No. 1 and FDC Red No. 3 in order to indicate older dental plaque in dark blue and newer dental plaque in violet-red; this provides important information in regard to the advancement of dental plaque formation and in regard to the treatment thereof.

U.S. Pat. No. 3,903,252, discloses an agent in gel form for making visible dental plaque that contains a pharmacologically harmless organic dye component that is selected from the class of FDC Red No. 3, FDC Blue No. 1, FDC Violet No. 1 and others.

U.S. Pat. No. 4,459,227, discloses a tooth paste containing FBC Blue No. 1 in order to make visible dental plaque. Japanese Patent No. 08059513 A, concerns a solution that contains, inter alia, Red No. 3 and other Reds for making visible dental plaque. The same holds true for Japanese Patent No. 08143477 A. U.S. Pat. No. 4,431,628 A, concerns a composition that contains the natural dye of sugar beets for making visible dental plaque.

European Patent No. 0 421 838, discloses agents for indicating dental plaque formation; the agents contain conventional water-soluble dye FDC Red No. 3. A disadvantage is that FDC Red No. 3 has an unpleasant taste; moreover, in the United States its use as a component of cosmetic products was prohibited in 1989 because its innocuousness had been called into question. According to European Patent No. 0 421 838 B1, the less bitter tasting dye FDC Red No. 40 has been proposed as a substitute dye; this dye has a stronger color intensity in comparison to other dental plaque-indicating agents, for example, FDC Blue No. 1, FDC Blue No. 2, so that these dyes are less useful as dental plaque-indicating agents than FDC Red No. 40.

U.S. Pat. No. 6,485,300, discloses an apparatus for detecting biological deposits on the surface of a tooth. The device has illumination means to direct exciting radiation onto a test tooth surface and detection means to detect fluorescence emission from the test tooth surface at a wavelength associated with that of auto fluorescence emission from clean tooth surface. The intensity of the said fluorescence emission from the test tooth surface is compared with an intensity of auto fluorescence emission from clean tooth surface and the comparison is associated with the presence of deposits on the test tooth surface. The device is preferably embodied in a toothbrush which indicates to the user that deposits are present and are being removed. The entire contents of each of which are incorporated herein by reference.

BRIEF SUMMARY OF THE INVENTION

The present invention provides a glow in the dark staining agent for staining dental plaque comprises: a first plaque-disclosant comprising a fluorophore having an fluorescence emission after being exposed to a light source, wherein the fluorophore adheres to tooth plaque; and a second plaque-disclosant comprising a dye particle that adheres to tooth plaque and is visible.

The present invention provides a method for producing a staining agent for staining dental plaque, the method comprising the steps of: combining phloxin B, lactose and magnesium stearate as a tableting agent; adding one or more dye compositions to the tableting agent; adding a fluorescent dye to the tableting agent; adding one or more flavoring agents to the tableting agent; and forming the tableting agent into a tablet.

The present invention provides a method of making dental plaque observable to the naked eye comprising the steps of providing teeth having plaque adhered thereto; contacting the teeth with a plaque-disclosant composition in a quantity effective, at a concentration to stain said plaque and render said plaque visible at wave lengths of light visible to said naked eye in the dark, wherein the plaque-disclosant composition comprises a first plaque-disclosant comprising a fluorophore having an fluorescence emission after being exposed to a light source, wherein the fluorophore adheres to tooth plaque and a second plaque-disclosant comprising a dye particle that adheres to tooth plaque and is visible; exposing the teeth to visible wavelengths of light; observing, with the naked eye, for any stained dental plaque on said teeth; and observing, with the naked eye, in dark conditions for any stained dental plaque, on said teeth.

The glow in the dark staining agent may be a tablet. The dye particle may be FDA Blue No. 1. The dye particle may be selected from amaranth (Red 2), erythrosine (Red 3), ponceau SX (Red 4), eosine (DC Red 22), phloxine (Red 28), allura red (Red 40), tartrazine (Yellow 5), quinoline yellow SS (DC Yellow 1), sunset yellow FCF (Yellow 6), quinoline yellow WS (DC Yellow 10), fast green FCF (Green 3), alizarine cyanine green F (DC Green 5), quinizarine, green SS (DC Green 6), brilliant blue FCF (Blue 1), indigo, and carmine (Blue 2). The staining agent further comprises lactose, phloxin B, magnesium stearate. The staining agent further comprises about 85 to 95% by weight lactose, about 1.5 to 2.6% by weight phloxin B; about 2.5 to 3.5% by weight FDA Blue No. 1; and about 0.15 to 0.25% by weight magnesium stearate. The fluorophore is selected from 1,3-Dihydro-1,3,3-trimethylspiro[2H-indole-2,3'-[3H]phenanthr[9,10-b](1,4-)oxazine]; bicyclo[2.2.1]hepta-2,5-diene; benzyl viologen dichloride; 4,4'-bipyridyl; 6-bromo-1',3'-dihydro-1',3',3'-trimethyl-8-nitrospiro[2H; 5-chloro-1,3-dihydro-1,3,3-trimethylspiro[2H-indole-2,3'-(3H)naphth[2,1-b-](1,4)oxazine]; 6,8-dibromo-1',3'-dihydro-1'3',3'-trimethylspiro[2H; 1,1'-diheptyl-4,4'-bipyridinium dibromide; 1',3'-dihydro-5'-methoxy-1',3',3'; 1',3'-dihydro-8-methoxy-1',3'3'-trimethyl-6-nitrospiro[2H]; 1',3'-dihydro-1',3',3'-trimethyl-6-nitrospiro[2H-1-benzopyran-2,2'-(2H)-in-dole]; 1,3-dihydro-1,3,3-trimethylspiro[2H-Indole-2,3'-[3H]naphtho[2,1-b][1-,4]oxazine]; 1,1'-dimethyl-4,4'-bipyridinium dichloride; 5-chloro-1,3-Dihydro-1,3,3-trimethylspiro[2H-indole-2,3'-(3H)phenanthr[9,-10-b](1,4)oxazine]; 5-methoxy-1,3,3-trimethylspiro[indoline-2,3'-[3H]naphtho[2,1-b]pyran]; and 2,3,3-trimethyl-1-propyl-3H-indolium iodide. The fluorophore may be selected from fluorescein, fluoresceine, resourcinolphthalein, rhodamine, imidazolium cations, pyridoimidazolium cations, dinitrophenyl, and tetramethylrhodamine.

BRIEF DESCRIPTION OF THE SEVERAL VIEWS OF THE DRAWINGS

For a more complete understanding of the features and advantages of the present invention, reference is now made to the detailed description of the invention along with the accompanying figures and in which:
None.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

For detection of plaque it is known to use two general methods for detecting dental plaque using fluorescence, secondary fluorescence and auto fluorescence. In secondary fluorescence teeth suspected of bearing plaque are treated with a fluorescent label material which preferentially binds to dental plaque, and after excess of the unbound material has been washed away from the teeth, the fluorescence emission, in response to illumination by exciting radiation, of the label material at areas of the tooth at which it has bound to plaque is detected to indicate the presence of dental plaque.

The present invention provides one or more plaque-disclosants, and specifically plaque-disclosants that glow in the dark. In addition, the one or more plaque-disclosants may include a combination of a first disclosant that can be seen in normal visible light and a second disclosant that can be seen in the absence of light or in low light. This allows multiple indications of the present of plaque.

The present invention also provides a method for detecting plaque in a multiplicity of light conditions. The plaque-disclosants may include a glow in the dark composition that provides an indicator in low, or no light conditions. In use, a child may brush his teeth using the plaque-disclosant of the present invention prior to bed-time. When the child is in bed or preparing for bed in a low light or dark room the parent may check the condition of the teeth to access the brushing technique. The presence of plaque will be indicated by the illumination of the glow in the dark plaque-disclosant. This provides an accurate and easy indication to asset the status of plaque on the teeth.

In addition, the present invention also provides a multiple indicator plaque-disclosant that allows both visible light indication and low or no light indication of the presence of plaque. The composition includes a first disclosant that can be seen in normal visible light and a second disclosant that can be seen in the absence of light, or in low light. This allows a child to brush his teeth and receive immediate feedback on the removal of plaque and his brushing technique. The parent can then check the condition of the teeth to assess the brushing technique when the child is in bed or preparing for bed in a low light or dark room. The presence of plaque will be indicated by the illumination of the glow in the dark plaque-disclosant. This allows the parent an immediate indication of the status of plaque on the teeth and in general the brushing technique.

The invention includes a dental plaque-disclosant composition for topical application in the oral cavity to permit detection of plaque formation which is not otherwise visually observable. The composition includes plaque-disclosants in the form of a staining agent (e.g., an organic dye, fluorescent dye or other coloring agent) and a fluorescent agent (e.g., an organic dye, fluorescent dye or other coloring agent) which selectively stains plaque formed on the teeth to render the plaque visually distinguishable and prominent from the enamel. The composition may also include thickening agents, flavoring agents, sweeteners and preservatives incorporated into the composition.

The present invention provides optical (e.g., color, change) orally acceptable plaque-disclosants, e.g., toothpaste, mouthwash, tablets and other compositions and methods for using the same. Plaque-disclosants of the present invention include fluorescent and colored plaque-disclosants and can serve multiple purposes. The plaque-disclosants of the present invention includes color/fluorescence indication and can be utilized as an entertaining and motivating means to encourage children to brush. The color/fluorescence plaque-disclosant can serve as a timing mechanism to provide children and parents a simple means to determine when an appropriate brushing duration has been completed. The color/fluorescence plaque-disclosant can be used as an indicating means for the diagnosis of an oral dysfunction. The color/fluorescence plaque-disclosant can be used as a diagnostic means to help determine whether an individual has a particular disease state expressed in the oral cavity. The color/fluorescence plaque-disclosant can be used as an alternative means for indicating the presence of an oral problem such as plaque buildup. The color/fluorescence plaque-disclosant can be sensitized by biochemical means to help serve as an indicator to the presence of tooth decay. The color/fluorescence plaque-disclosant can be used as a means to help correct deficiencies in brushing technique.

The invention has the object of providing plaque-disclosant that includes a fluorescent and/or staining agent that is available in tablet, liquid or paste form and is therefore especially suitable for screening, for example, in schools and homes, that with regard to health considerations is harmless, and that is able to indicate older dental plaque as well as newer dental plaque. tablet, liquid or paste form.

For example, a staining agent in tablet, liquid or paste form for making visible dental plaque is proposed that contains lactose in a range of approximately 85 to 95% by weight, phloxin B in the range of approximately 1.5 to 2.6% by weight, FDA Blue No. 1 in the range of approximately 2.5 to 3.5% by weight as well as magnesium stearate in the range of 0.15 to 0.25% by weight and a fluorescent dye composition. By using phloxin B in addition to FDA Blue No. 1, it is achieved that older dental plaque is shown in dark blue and newer dental plaque is shown in violet-red. In the dark environment the fluorescent dye will indicate the presence of dental plaque. Aside from the medical indication for a dentist, the staining agent according to the invention that is in tablet form can be used independent of a dental examination also by individuals as an indicator for dental plaque formation so that it practically provides also a cosmetic function.

The present invention provides a light glow/emitting composition that can be formulated using a single component or a multiple component composition. For example, a standard translucent toothpaste base is desirable so that good illumination and emission can be accomplished. And in the form of a tablet rapid dissolving with good illumination and emission characteristics. Photo-luminescent compounds including zinc sulfide or strontium aluminate activated by europium can be mixed directly with the toothpaste composition. Normal room light, sunlight or various electrical light sources can be used to illuminate the pigment. The pigment will emit light for a period of time following the illumination charging effect. The duration of illumination can be used as a means for determining brushing duration.

The present invention provides a light glow/emitting composition with fluorescence activation and can be in the form of toothpaste, mouthwash, tablet or other composition. For example, the composition may include a fluorescence dye such as fluoresceine, rhodamine, imidazolium, or the like mixed into the base. Upon dispersion, the fluorescent dye can be dispersed and available for fluorescence excitation using an illumination source. An illuminating source may be used with a compatible light source such as a UV light emitting diode (300-400 nanometers) capable of exciting the fluorescence dye. The appearance of fluorescence emission during brushing can be used as a means for determining brushing duration. The second visible dye component may be visualized under normal conditions.

Dyes (i.e. dyes responsive to an electromagnetic, such as visible light, stimulus) can find use in a variety of color change mediums and formats. Photochromic materials can include but are not limited to dyes including: 1,3-Dihydro-1,3,3-trimethylspiro[2H-indole-2,3'-[3H]phenanthr[9,10-b] (1,4-)oxazine]; bicyclo[2.2.1]hepta-2,5-diene; benzyl viologen dichloride; 4,4'-bipyridyl; 6-bromo-1',3'-dihydro-1',3',3'-trimethyl-8-nitrospiro[2H; 5-chloro-1,3-dihydro-1,3,3-trimethylspiro[2H-indole-2,3'-(3H)naphth[2,1-b-](1,4) oxazine]; 6,8-dibromo-1',3'-dihydro-1'3',3'-trimethylspiro [2H; 1,1'-diheptyl-4,4'-bipyridinium dibromide; 1',3'-dihydro-5'-methoxy-1',3',3; 1',3'-dihydro-8-methoxy-1',3'3'-trimethyl-6-nitrospiro[2H]; 1',3'-dihydro-1'3',3'-trimethyl-6-nitrospiro[2H-1-benzopyran-2,2'-(2H)-in-dole]; 1,3-dihydro-1,3,3-trimethylspiro[2H-Indole-2,3'-[3H]naphth[2,1-b][1-,4]oxazine]; 1,1'-dimethyl-4,4'-bipyridinium dichloride; 5-chloro-1,3-Dihydro-1,3,3-trimethylspiro[2H-indole-2,3'-(3H)phenanthr[9,-10-b](1,4)oxazine]; 5-methoxy-1,3,3-trimethylspiro[indoline-2,3'-[3H]naphtho [2,1-b]pyran]; 2,3,3-trimethyl-1-propyl-3H-indolium iodide and the like. Fluorescent dyes can find use in various color activation toothpaste mediums and formats. Fluorescent dye compounds can include but are not limited to: fluorescein, fluoresceine, resourcinolphthalein, rhodamine, imidazolium cations, pyridoimidazolium cations, dinitrophenyl, tetramethylrhodamine and the like. A wide range of fluorescent dyes that can be activated at various wavelengths and emit light at lower wavelengths can be purchase.

Encapsulated food colors can be masked with an opaque encapsulating material, formed in small micro-crystals prior to release, obscured using lake dye pigments, impregnated in opaque waxes or the like. The initially treated dye can be processed such that a physical or chemical means can transform the initial colored state to a second colored state. Typical dyes include: amaranth (Red 2), erythrosine (Red 3), ponceau SX (Red 4), eosine (DC Red 22), phloxine (Red 28), allura red (Red 40), tartrazine (Yellow 5), quinoline yellow SS (DC Yellow 1), sunset yellow FCF (Yellow 6), quinoline yellow WS (DC Yellow 10), fast green FCF (Green 3), alizarine cyanine green F (DC Green 5), quinizarine, green SS (DC Green 6), brilliant blue FCF (Blue 1), indigo, carmine (Blue 2) and the like.

A two-component plaque-disclosant can be prepared. The first component can contain fluorescein, a visible dye and phenyl oxalate. The second paste component can contain a hydrogen peroxide solution. When the two components are mixed, a chemi-luminescent reaction can occur whereby visible light can be emitted from the fluorescein present. Mixing at elevated temperatures (body temperature) can increase the illumination intensity. The solution concentrations of fluorescein can be controlled to indicate a one to several minute brushing time.

A light glow/emitting tablet, liquid or paste can be formulated using a single component. A standard translucent base is desirable so that good illumination and emission can be accomplished. Photo-luminescent compounds including zinc sulfide or strontium aluminate activated by europium can be mixed directly with the toothpaste composition. Normal room light, sunlight or various electrical light sources can be used to illuminate the pigment. The pigment will emit light for a period of time following the illumination charging effect. The duration of illumination can be used as a means for determining brushing duration.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method of making dental plaque observable to the naked eye in both dark conditions and light conditions comprising the steps of:
   providing teeth having plaque adhered thereto;
   contacting the teeth with a plaque-disclosant composition in a quantity effective to stain said plaque and render said plaque visible at wave lengths of light visible to said naked eye in the dark, wherein the plaque-disclosant composition comprises;
   a first fluorescent plaque-disclosant comprising a fluorescein that adheres to tooth plaque, and
   a second fluorescent plaque-disclosant comprising a rhodamine that adheres to tooth plaque,
   a visible plaque-disclosant comprising lactose, phloxin B, magnesium stearate and a dye particle that adheres to tooth plaque and is visible;
   exposing the teeth to one or more visible wavelengths of light;
   exciting the fluorescein with the one or more visible wavelengths of light;
   releasing a fluorescein emission from the fluorescein at a first emission wavelength as a result of the step of exciting;
   adsorbing the fluorescein emission by the rhodamine;
   releasing a rhodamine emission from the rhodamine at a second emission wavelength as a result of the step of adsorbing the fluorescein emission;
   identifying the visible plaque-disclosant on said teeth to identify plaque;
   reducing the light level; and
   identifying the rhodamine emission on said teeth to identify plaque on said teeth.

2. The composition of claim 1, wherein the plaque-disclosant composition further comprises about 85 to 95% by weight lactose, about 1.5 to 2.6% by weight phloxin B; about 2.5 to 3.5% by weight FDA Blue No. 1; and about 0.15 to 0.25% by weight magnesium stearate.

* * * * *